United States Patent
Lee et al.

(10) Patent No.: US 11,098,379 B2
(45) Date of Patent: Aug. 24, 2021

(54) COMPOSITION FOR DETECTING POTATO VIRUS Y INCLUDING M13KO7 BACTERIOPHAGE AND KIT INCLUDING THE SAME

(71) Applicants: Research & Business Foundation Sungkyunkwan University, Suwon-si (KR); Republic of Korea (Management: Rural Development Administration), Jeonju-si (KR)

(72) Inventors: Suk-Chan Lee, Suwon-si (KR); Sang-Ho Cho, Gunpo-si (KR); Young-Gyu Lee, Gangneung-si (KR)

(73) Assignees: Research & Business Foundation Sungkyunkwan University, Suwon-si (KR); Republic of Korea (Management: Rural Development Administration), Jeonju-si (KR)

( * ) Notice: Subject to any disclaimer, the term of this patent is extended or adjusted under 35 U.S.C. 154(b) by 151 days.

(21) Appl. No.: 16/556,791

(22) Filed: Aug. 30, 2019

(65) Prior Publication Data
US 2020/0071775 A1 Mar. 5, 2020

(30) Foreign Application Priority Data
Sep. 3, 2018 (KR) .......................... 10-2018-0104618

(51) Int. Cl.
*C12Q 1/6895* (2018.01)
*C12Q 1/70* (2006.01)
*C12N 7/00* (2006.01)
*G01N 33/569* (2006.01)

(52) U.S. Cl.
CPC .............. *C12Q 1/6895* (2013.01); *C12N 7/00* (2013.01); *C12Q 1/701* (2013.01); *G01N 33/56983* (2013.01); *C12N 2795/14111* (2013.01); *G01N 2333/01* (2013.01)

(58) Field of Classification Search
None
See application file for complete search history.

(56) References Cited

U.S. PATENT DOCUMENTS 6,132,722 A * 10/2000 Siemers ............. A61K 47/6891
424/192.1
2020/0071775 A1 * 3/2020 Lee ....................... C07K 14/005

OTHER PUBLICATIONS

Alignment of instant SEQ ID No. 1 with geneseq db acc No. AAU81745 in WO200198366 Dec. 2001 by Ley et al.*
Alignment of instant SEQ ID No. 2 with geneseq db acc No. AZI96893 in WO2011069993 Aug. 2011 by Somers et al.*
Alignment of instant SEQ ID No. 3 with geneseq db acc No. AAB35094 in Jun. 2007 by Janda et al.*
(Continued)

*Primary Examiner* — Shanon A. Foley
(74) *Attorney, Agent, or Firm* — NSIP Law

(57) ABSTRACT

The present disclosure relates to a composition for detecting a potato virus Y including an M13KO7 bacteriophage and a kit including the same. Since the M13KO7 bacteriophage of the present disclosure may be easily produced using *E. coli* and is a large aggregate of proteins, the M13KO7 bacteriophage is more stable than antibodies even when exposed to external physical or chemical factors. Therefore, the composition of the present disclosure has an effect of diagnosing only the PVY specifically and accurately and may be usefully used in related industries.

3 Claims, 5 Drawing Sheets

Specification includes a Sequence Listing.

(56) References Cited

OTHER PUBLICATIONS

Alignment of instant SEQ ID No. 4 with geneseq db acc No. AAR04003 in WO9002809 Jun. 2007 by Ladner et al.*
Alignment instant of SEQ ID No. 5 with geneseq db acc No. AAB35095 in WO200071694 Jun. 2007 by Janda et al.*
Alignment of instant SEQ ID No. 1 with geneseq db acc No. BBW87040 in WO2015046554 May 2015 by Ishii.*
Vieira et al. "Production of single-stranded plasmid DNA." Recombinant DNA Methodology (1989): 225-233).*
Rouis et al. (Journal of Virological Methods. 2006; 137: 1-6).*
Leonard et al. (Journal of Immunological Methods. 2007; 323: 172-179).*
Boonham et al. (Journal of Virological Methods. 1998; 74: 193-199).*
Erdag et al.. ("Production of recombinant antibody against potato virus Y by using phage display technology." Biotechnology & Biotechnological Equipment. 2000; 14 (1): 18-24).*

* cited by examiner

[Fig. 1a]
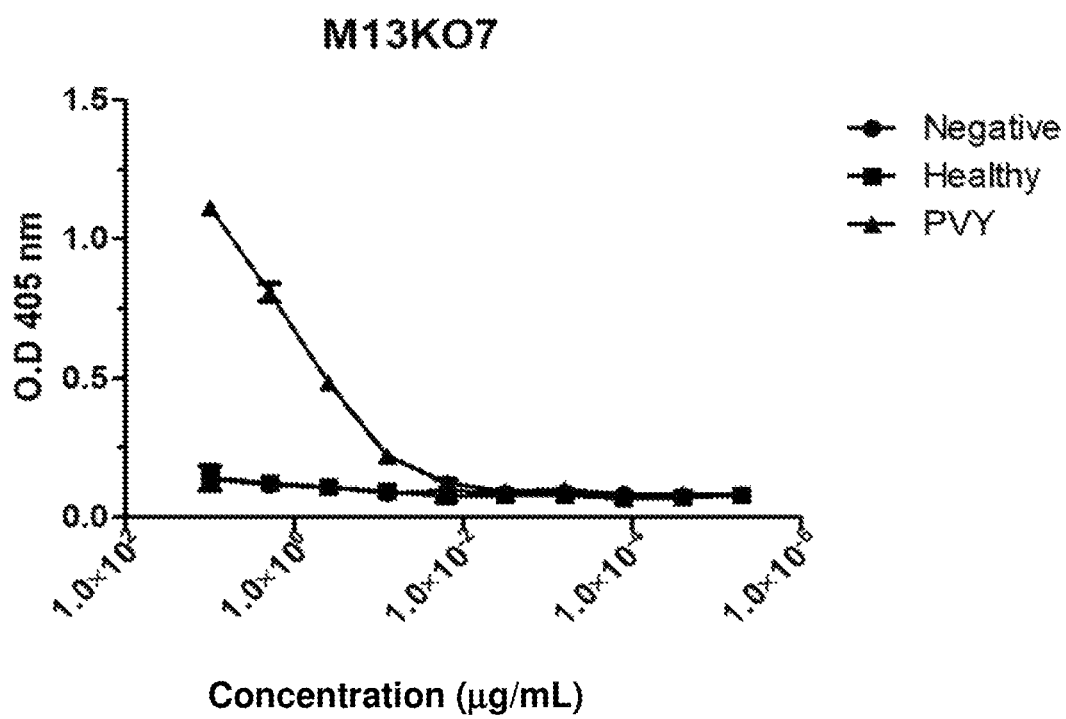

[Fig. 1b]
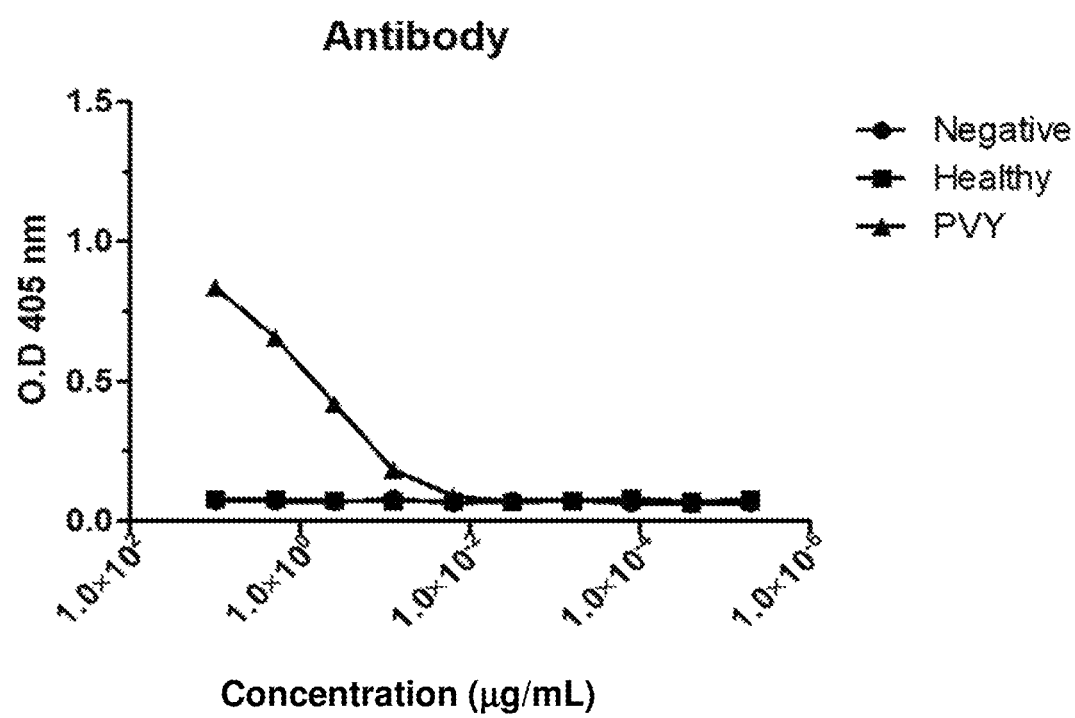

[Fig. 1c]
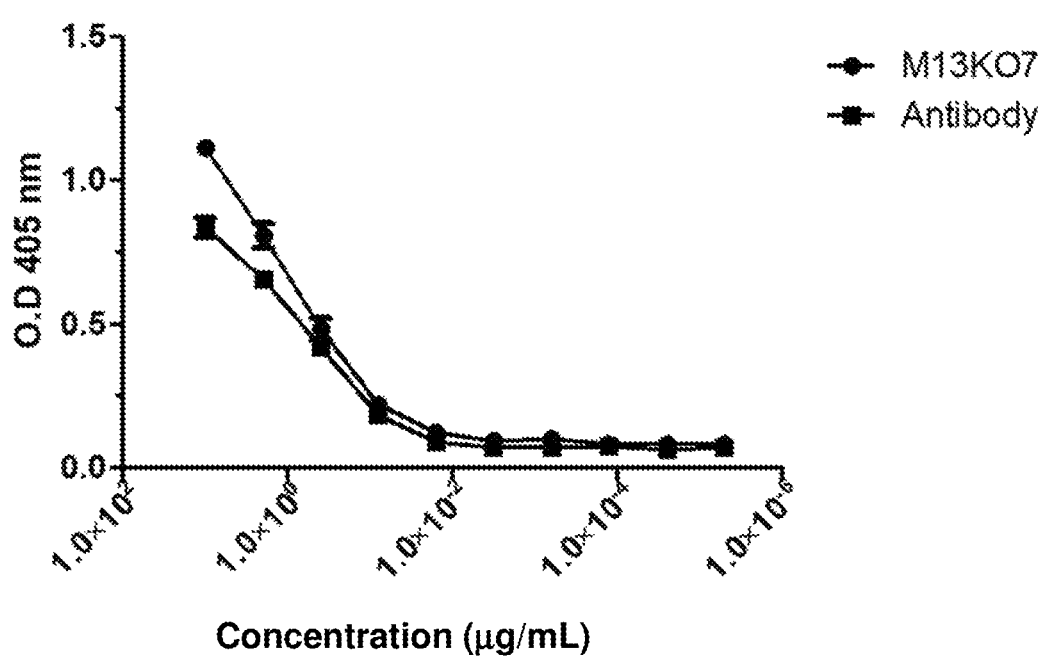

[Fig. 2]
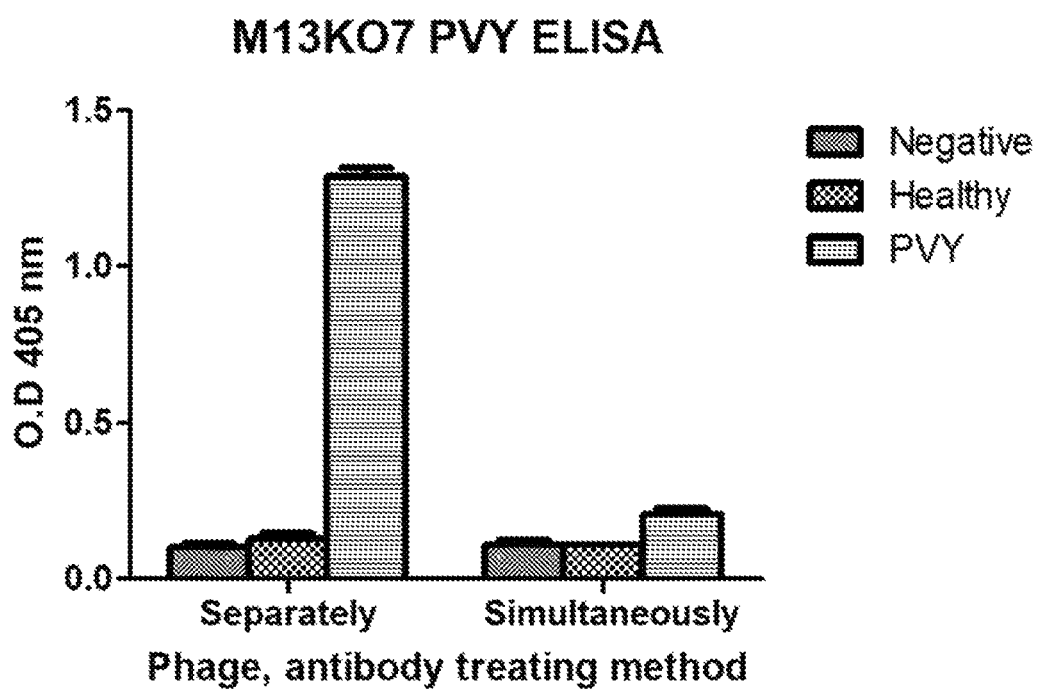

[Fig. 3]
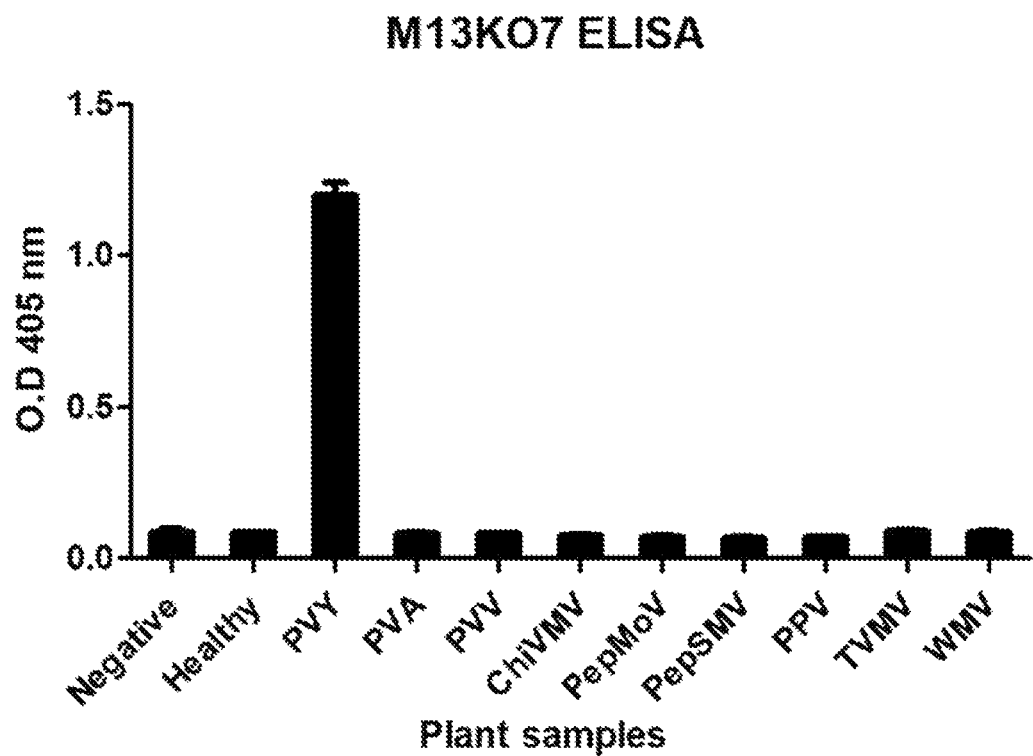

COMPOSITION FOR DETECTING POTATO VIRUS Y INCLUDING M13KO7 BACTERIOPHAGE AND KIT INCLUDING THE SAME

CROSS-REFERENCE TO RELATED APPLICATION

This application is based on and claims priority from Korean Patent Application No. KR 10-2018-0104618, filed on Sep. 3, 2018, with the Korean Intellectual Property Office, the disclosure of which is incorporated herein in its entirety by reference.

TECHNICAL FIELD

The present disclosure relates to a composition for detecting a potato virus Y including an M13KO7 bacteriophage and a kit including the same.

BACKGROUND

A potato virus Y (PVY) belongs to the viral group of potyviridae, a virus that is easily infected with other crops as well as potatoes to cause large economic losses. The PVY is easily transferred to machines, carriers, or environmental means in all regions where host crops can grow, and losses in potato production vary from 30% to 80%, depending on a potato cultivar and a type of virus. Potato virus strains are generally divided into $PVY^O$, $PVY^C$ and $PVY^N$. The $PVY^O$ is a type to be infected mostly in countries that produce potatoes. This infection of PVY causes potato plants to show necrosis, staining, and yellowing of leaves.

Plant viruses, including the potato virus Y (PVY) are almost impossible to cure the disease, and the spread of viruses causes great damage to domestic food resources, such as reducing the marketability of the crops and reducing yield of crops or causes fatal losses to farmers (Potato, Viruses, and Seed Certification in the USA to Provide Healthy Propagated Tubers, Halterman at al., 2012, Agricultural Sciences). The research direction of these plant viruses is focused on diagnosis rather than treatment, and this diagnosis technique requires a fast and accurate diagnosis technique because an initial response is important. Methods for diagnosing plant viruses include a method for amplification and diagnosis of viral nucleic acids based on polymerase chain reaction (PCR) and a method for serological analysis using antibodies such as enzyme-linked immunosorbent assay (ELISA). However, these antibodies require the sacrifice of laboratory animals for producing and may be easily lost their activity due to external physical or chemical factors, thereby making it difficult to produce or handle the antibodies in the laboratory of studying plant viruses or in sites requiring diagnosis.

Since an M13KO7 bacteriophage may be easily produced using E. coli and is a large aggregate of proteins, the M13KO7 bacteriophage is more stable than antibodies even when exposed to external physical or chemical factors. However, M13KO7 bacteriophage was a common method used as an auxiliary means for producing a phage display library. As a diagnosis method provided by the present disclosure, the present disclosure has been completed to specifically and effectively detect PVY in potato plant samples using specific reaction phenomena of two viruses, PVY and M13KO7 bacteriophage.

SUMMARY

The present disclosure has been made in an effort to provide a composition for detecting a potato virus Y (PVY) including an M13KO7 bacteriophage.

Further, the present disclosure has been made in an effort to provide a kit for detecting a PVY including the composition.

Further, the present disclosure has been made in an effort to provide a method for detecting a PVY including reacting the composition with a desired sample.

An exemplary embodiment of the present disclosure provides a composition for detecting a potato virus Y (PVY) including an M13KO7 bacteriophage.

Another exemplary embodiment of the present disclosure provides a kit for detecting a PVY including the composition.

Yet another exemplary embodiment of the present disclosure provides a method for detecting a PVY including reacting the composition with a desired sample.

The present disclosure relates to a composition for detecting potato virus Y including an M13KO7 bacteriophage and a kit including the same. Since the M13KO7 bacteriophage of the present disclosure may be easily produced using E. coli and is a large aggregate of proteins, the M13KO7 bacteriophage is more stable than antibodies even when exposed to external physical or chemical factors. Therefore, the composition of the present disclosure has an effect of diagnosing only the PVY specifically and accurately and may be usefully used in related industries.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

FIGS. 1a, 1b, and 1c are diagrams of confirming a detection capacity (FIG. 1c) for a PVY infected strain by comparing M13KO7 bacteriophage (FIG. 1a) with a conventional PVY detection antibody (FIG. 1b).

FIG. 2 is a diagram of confirming results of quantitatively measuring a detection capacity of a PVY infected strain for M13KO7 bacteriophage in accordance with a simplified diagnostic method (Separately is a group treated with a phage and a detection antibody separately, and Simultaneously is a group treated with a phage and a detection antibody simultaneously).

FIG. 3 is a diagram illustrating results of quantitatively measuring that an M13KO7 bacteriophage of the present disclosure specifically detects a PVY infected strain among several potyviruses.

DETAILED DESCRIPTION

In the following detailed description, reference is made to the accompanying drawing, which forms a part hereof. The illustrative embodiments described in the detailed description, drawings, and claims are not meant to be limiting. Other embodiments may be utilized, and other changes may be made, without departing from the spirit or scope of the subject matter presented here.

The present disclosure provides a composition for detecting a potato virus Y (PVY) including an M13KO7 bacteriophage.

In the present disclosure, the term "bacteriophage" is referred to as a phage as a virus that is infected with bacteria and grows only in its cells, and the bacteriophage is a microscopic particle that passes through a bacterial filter and cannot be seen directly by an optical microscope and can grow only in living cells.

The detection may be performed in at least one sample selected from the group consisting of potato (*Solanum* sp.), eggplant (*Solanum* sp.), tobacco (*Nicotiana* sp.), tomato (*Lycopersicon* sp.), pepper (*Capsicum* sp.), dahlia (*Dahlia* sp.) and *petunia*, preferably potato, but is not limited thereto.

The M13KO7 bacteriophage may be encoded by a base sequence represented by SEQ ID NO: 11. Preferably, the M13KO7 bacteriophage is at least one selected from the group consisting of amino acids represented by SEQ ID NO: 1, SEQ ID NO: 2, SEQ ID NO: 3, SEQ ID NO: 4, and SEQ ID NO: 5, and the amino acid is a capsid protein of M13KO7 bacteriophage, but is not limited thereto.

The amino acids represented by SEQ ID NO: 1, SEQ ID NO: 2, SEQ ID NO: 3, SEQ ID NO: 4 and SEQ ID NO: 5 may be coded by base sequences represented by SEQ ID NO: 6, SEQ ID NO: 7, SEQ ID NO: 8, SEQ ID NO: 9, and SEQ ID NO: 10, but is not limited thereto.

The range of amino acids according to the present disclosure includes proteins having amino acid sequences represented by SEQ ID NO: 1, SEQ ID NO: 2, SEQ ID NO: 3, SEQ ID NO: 4, and SEQ ID NO: 5 and functional equivalents of the proteins. The "functional equivalent" has sequence homology of at least 70% or more, preferably 80% or more, more preferably 90% or more, much more preferably 95% or more with the amino acid sequence represented by the SEQ ID NOs as a result of the addition, substitution or deletion of the amino acid and refers to a protein having substantially homogeneous physiological activity with the protein represented by the SEQ ID Nos. In amino acids of the present disclosure, amino acid sequence variants thereof as well as proteins having native amino acid sequences thereof are within the scope of the present disclosure.

The amino acid variant refers to a protein having a different sequence from the native amino acid sequence by deletion, insertion, non-conservative or conservative substitution, or a combination thereof of at least one amino acid residue. Amino acid exchanges in proteins and peptides in which the activity of the molecule is entirely not changed are known in the art (H. Neurath, R. L. Hill, The Proteins, Academic Press, New York, 1979). In addition, tetrapeptides or variants thereof may be extracted from nature or synthesized (Merrifield, J. Amer. Chem. Soc. 85: 2149-2156, 1963) or may be prepared by a genetic recombination method based on DNA sequences (Sambrook et al, Molecular Cloning, Cold Spring Harbor Laboratory Press, New York, USA, 2nd edition, 1989).

The amino acid variant is made based on the relative similarity of an amino acid side-chain substituent, such as hydrophobicity, hydrophilicity, charges, sizes and the like. By analysis of the size, shape and type of the amino acid side-chain substituent, it can be seen that arginine, lysine and histidine are all positively charged residues; alanine, glycine and serine have similar sizes; and phenylalanine, tryptophan and tyrosine have similar shapes. Thus, based on these considerations, arginine, lysine and histidine; alanine, glycine and serine; and phenylalanine, tryptophan and tyrosine may be biologically functional equivalents.

In introducing mutation, a hydrophobic index of amino acids may be considered. Each amino acid is assigned with a hydrophobic index according to its hydrophobicity and charges: isoleucine (+4.5); valine (+4.2); leucine (+3.8); phenylalanine (+2.8); cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The hydrophobic amino acid index is very important in assigning an interactive biological function of the proteins. It is known that substitution with amino acids having similar hydrophobic indexes may retain similar biological activity. When introducing mutations with reference to the hydrophobic index, substitution is made between amino acids which exhibit a hydrophobic index difference, preferably within ±2, more preferably within ±1, and much more preferably within ±0.5.

On the other hand, it is also well known that substitutions between amino acids having similar hydrophilic values result in proteins with equivalent biological activity. As disclosed in U.S. Pat. No. 4,554,101, the following hydrophilic values are assigned to each amino acid residue: arginine (+3.0); lysine (+3.0); asphaltate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

When introducing mutations with reference to the hydrophilic value, substitution is made between amino acids which exhibit a hydrophilic value difference, preferably within ±2, more preferably within ±1, and much more preferably within ±0.5.

Amino acid exchange in proteins without entirely changing the activity of the molecule is known in the art (H. Neurath, R. L. Hill, The Proteins, Academic Press, New York, 1979). The most commonly occurring exchange is an exchange between amino acid residues Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu, and Asp/Gly.

Variants of the base sequence constituting the M13KO7 bacteriophage are included within the scope of the present disclosure. Base sequences that may be used as genes encoding amino acids or proteins of the present disclosure include functional equivalents of the base sequences constituting the M13KO7 bacteriophage, for example, variants in which some of the base sequences are modified by deletion, substitution or insertion, but may functionally act identically with the base sequences. Specifically, the variants may include base sequences having sequence homology of 70% or more, more preferably 80% or more, much more preferably at 90% or more, and most preferably 95% or more with the base sequences constituting the M13KO7 bacteriophage. The "% of sequence homology" to the base sequence is determined by comparing two optimally arranged sequences with a comparison region, in which a part of a base sequence in the comparison region may include addition or deletion (i.e., gap) compared with a reference sequence (not including addition or deletion) for the optimal alignment of the two sequences.

In one embodiment of the present disclosure, the M13KO7 bacteriophage of the present disclosure is proliferated by inoculating with *E. coli* strains in a medium and infecting the M13KO7 bacteriophage. Then, as a result of comparing PVY binding capacities of a conventional PVY antibody and the M13KO7 bacteriophage of the present disclosure, it was confirmed that the M13KO7 bacteriophage had more improved sensitivity than the conventional antibody at the same concentration. In addition, compared to ChiVMV, PepMoV, PepSMV, PVA, PVV, PVMV, WMV and PPV belonging to the potyvirus, it was confirmed that the specificity and accuracy for PVY was excellent. In addition, there is an effect that can detect the PVY even with the M13KO7 bacteriophage of the present disclosure even without a capture antibody.

The term "culture" in the present disclosure means to grow microorganisms under environmental conditions that are appropriately artificially controlled.

The M13KO7 bacteriophage of the present disclosure can be grown in a general medium, and the medium contains nutrients required by an object to be cultured. The medium may also be referred to as an incubator or a culture solution, and includes a natural medium, a synthetic medium, or a selective medium.

The medium used for culture needs to meet the requirements of a specific strain in an appropriate manner while controlling a temperature, pH, etc. in a general medium containing appropriate carbon sources, nitrogen sources, amino acids, vitamins and the like. As the carbon source to be used, mixed sugars of glucose and xylose are used as a main carbon source, and in addition, the carbon source includes sugars and carbohydrates such as sucrose, lactose, fructose, maltose, starch and cellulose, oils and fats such as soybean oil, sunflower oil, castor oil, and coconut oil, fatty acids such as fat, palmitic acid, stearic acid, and linoleic acid, alcohols such as glycerol and ethanol, and organic acids such as acetic acid. These materials may be used individually or as a mixture. The nitrogen source to be used may use inorganic nitrogen sources such as ammonia, ammonium sulfate, ammonium chloride, ammonium acetate, ammonium phosphate, ammonium carbonate, and ammonium nitrate; and organic nitrogen sources including amino acids and peptones such as glutamic acid, methionine, and glutamine, NZ-amine, meat extract, yeast extract, malt extract, corn steep liquor, casein hydrolyzate, fish or decomposition products thereof, and defatted soybean cake or decomposition products thereof. These nitrogen sources may be used alone or in combination. The medium may include monopotassium phosphate, dipotassium phosphate and corresponding sodium-containing salts as a phosphate source. As the phosphate source to be used, potassium dihydrogen phosphate or dipotassium hydrogen phosphate, or corresponding sodium-containing salts. In addition, as the inorganic compound, sodium chloride, calcium chloride, iron chloride, magnesium sulfate, iron sulfate, manganese sulfate and calcium carbonate may be used. Finally, in addition to the materials, required growth substances such as amino acids and vitamins may be used.

In addition, precursors suitable to the culture medium may be used. The raw materials may be added by a batch, fed-batch or continuous method in a suitable manner to the culture in the culture process, but is not particularly limited thereto. Basic compounds such as sodium hydroxide, potassium hydroxide, ammonia or acid compounds such as phosphoric acid or sulfuric acid may be used in an appropriate manner to adjust the pH of the culture.

Further, the present disclosure provides a kit for detecting a PVY including the composition.

The kit may be performed by at least one selected from the group consisting of enzyme-linked immunosorbent assay (ELISA), western blotting, immunofluorescence, immunohistochemistry staining, flow cytometry, immunocytochemistry, radioimmunoassay (RIA), immunoprecipitation assay, immunodiffusion assay, complement fixation assay, and protein chips, and preferably ELISA, but is not limited thereto.

The ELISA may perform direct ELISA, indirect ELISA, or sandwich ELISA, but is not limited thereto, in order to detect the PVY using the composition.

Further, the present disclosure provides a method for detecting a PVY including reacting the composition with a desired sample.

The sample is at least one selected from the group consisting of potato (*Solanum* sp.), eggplant (*Solanum* sp.), tobacco (*Nicotiana* sp.), tomato (*Lycopersicon* sp.), pepper (*Capsicum* sp.), dahlia (*Dahlia* sp.) and *petunia*, and preferably potato, but is not limited thereto.

Hereinafter, the present disclosure will be described in more detail with reference to the following Examples. However, the following Examples are only intended to embody the contents of the present disclosure, and the present disclosure is not limited thereto.

[Preparation Example 1] Proliferation of M13KO7 Bacteriophage

In order to proliferate an M13KO7 bacteriophage used in the present disclosure, 1% *E. coli* strain XL1-blue was inoculated in a 2TY broth medium containing tetracycline (10 μg/ml) and 2% glucose (v/v) and then incubated in a stirring incubator at 37° C. until an OD600 nm value became 0.6 or more. Thereafter, the M13KO7 bacteriophage was infected with an amount of 50 multiplicity of infection (MOI) and then left without stirring at 37° C. for 30 minutes. After the cells were settled using a centrifuge, a supernatant was discarded, and a pellet was incubated in a new 2TY broth medium. The new medium contained tetracycline (10 μg/ml), kanamycin (50 μg/ml), and 0.2% glucose (v/v) and was incubated in a stirring incubator at 30° C. for 24 hours. After incubation, the cells were settled using a centrifuge and a supernatant was taken and filtered using a 0.22 μm stericup (Millipore). ⅕ volume of PEG/NaCl (20% polyethylene glycol 6000, 2.5 M NaCl) was added to a filtrate and mixed well and reacted in ice for 1 hour to aggregate a phage. After the phage was sufficiently settled using a high-speed centrifuge, the supernatant was removed, and the phage was mixed with a phosphate-buffered saline (PBS; pH 7.4) solution. For long-term storage, 1 volume of glycerol was added and stored at −20° C.

[Preparation Example 2] Preparation of Potato Virus Y (PVY) Potato

Potato plant samples infected with a potato virus were kindly provided from the national institute of highland agriculture of the National Institute of Crop Science (KRI) and used for experiments. The plant samples were frozen at −86° C., juiced by a required amount for a certification experiment, and then mixed with a general extraction buffer (solution prepared by mixing 10 mM sodium sulfite, 2% (w/v) polyvinylpyrrolidone (MW 40,000), 0.2% (w/v) sodium azide, 2% (w/v) bovine serum albumin (BSA), and 2% (v/v) tween-20 (Promega) with PBS (pH 7.4)).

[Example 1] Confirmation of PVY Binding Capacity Using M13KO7 Bacteriophage and Comparison with Antibodies In order to confirm a binding capacity of a PVY with an M13KO7 bacteriophage, an ELISA experiment was conducted. A PVY capture antibody (Agdia) was diluted at a concentration of 0.1 µg/ml in a carbonate coating buffer (15 mM sodium carbonate, 35 mM sodium bicarbonate, pH 9.6) and dispensed by 100 µl into wells of a 96 well ELISA plate, and then reacted for 4 hours at room temperature. After the antibody coating reaction, the plate was washed three times using tris-buffered saline (TBS; pH 7.4) containing 0.1% (v/v) tween-20 as a washing buffer (TBS-T). Subsequently, samples of a negative control group (general extraction buffer), a healthy strain, and a PVY infected strain were prepared for general extraction as described in Preparation Example 2 and dispensed by 100 µl per each well, and then reacted with a virus at 4° C. for 16 hours. In order to compare the binding strength with existing antibodies, PVY capture antibody and plant samples were prepared in the same manner as described above on an extra plate. After washing all plates 6 times with TBS-T, in one plate, an M13KO7 bacteriophage was diluted at a concentration of 3 µg/ml in TBS-T containing 3% BSA and dispensed by 100 µl per each well. In the other plate, a PVY detection antibody (Agdia) was diluted to a concentration of 3 µg/ml in TBS-T containing 3% BSA and dispensed by 100 µl per each well, and all the plates reacted with a virus for 1 hour at room temperature. After washing all the plates 3 times with TBS-T, in the plate reacted with the M13KO7 bacteriophage, an anti-M13 HRP conjugated antibody (Sino biological) was diluted to a concentration of 3 µg/ml in TBS-T containing 3% BSA and dispensed by 100 µl per each well. In the other plate, an anti-mouse IgG HRP conjugated antibody (Cell signaling technology) was diluted to a concentration of 3 µg/ml in TBS-T containing 3% BSA and dispensed by 100 µl per each well, and all the plates reacted for 1 hour at room temperature. After washing all the plates 6 times, in all the plates, 100 µl of a 3,5',5,5'-tetramethylbenzidine (TMB) solution was added to each well to perform color development and after 10 minutes, 100 µl of 1 M sulfuric acid was added to stop the color development. The binding capacity of M13KO7 bacteriophage and PVY was measured quantitatively by using a spectrophotometer, and the binding strength with the antibody used in the ELISA assay was compared.

As illustrated in FIGS. 1a, 1b, and 1c, it was confirmed that the detection capacity of the PVY infected strain using the M13KO7 bacteriophage showed about 25% improved sensitivity at the same concentration compared to the existing antibody.

[Example 2] Confirmation of Optimization Conditions of PVY Infected Strain Assay Method Using M13KO7 Bacteriophage An assay method was optimized to more effectively detect a PVY infected strain using an M13KO7 bacteriophage. More specifically, samples of a negative control group, a healthy strain, and a PVY infected strain were prepared in general extraction as described in Preparation Example 2 without reacting a capture antibody in a 96 well plate and dispensed by 100 µl per each well, and then reacted at 4° C. for 16 hours. After washing all plates 6 times with TBS-T, in one plate, an M13KO7 bacteriophage was diluted to a concentration of 3 µg/ml in TBS-T containing 3% BSA and dispensed by 100 µl per each well, and then reacted for 1 hour at room temperature. After washing the corresponding plate 3 times with TBS-T, an anti-M13 HRP conjugated antibody (Sino biological) was diluted to a concentration of 3 µg/ml in TBS-T containing 3% BSA and dispensed by 100 µl per each well, and then reacted for 1 hour at room temperature. In addition, in the other plate, the M13KO7 bacteriophage and the anti-M13 HRP conjugated antibody (Sino biological) were diluted to a concentration of 3 µg/ml and then mixed and dispensed by 100 µl per each well, and then reacted for 2 hours 30 minutes at room temperature. After washing all the plates 6 times, in all the plates, 100 µl of a TMB solution was added to each well of all the plates to perform color development and after 10 minutes, 100 µl of 1 M sulfuric acid was added to stop the color development. The binding capacity of the M13KO7 bacteriophage and the PVY was measured quantitatively by using a spectrophotometer, and experiments of reacting the HRP conjugated antibody separately from the phage and reacting the HRP conjugated antibody simultaneously with the phage were compared.

As illustrated in FIG. 2, it was confirmed that the group treated with the HRP conjugated antibody separately from the M13KO7 bacteriophage detected the PVY infected strain more accurately and showed an accurate detection result without a capture antibody.

[Example 3] Confirmation of PVY Infected Strain-Specific Detection of M13KO7 Bacteriophage In order to confirm whether an M13KO7 bacteriophage specifically detects a PVY infected strain, a certification experiment with a potyvirus to which the PVY belongs was performed. Specifically, the potyvirus used in the experiment was distributed by the plant virus group bank (PVGB) of the Seoul Women's University and experimented, and the distributed virus was chili veinal mottle virus (ChiVMV; PV-0897), pepper mottle virus (PepMoV; PV-1113), pepper severe mosaic virus (PepSMV; PV-1191), potato virus A (PVA; PV-0827), potato virus V (PVV; PV-0827), tobacco vein mottling virus (PVMV; PV-0251), and watermelon mosaic virus (WMV; PV-0393) which were lyophilized. In addition, a certification experiment for a plum pox virus (PPV) retained in the laboratory was conducted. All potyviruses including the PVY were prepared in a general extraction buffer as described in Preparation Example 2, dispensed by 100 µl per each well, and then reacted with the virus at 4° C. for 16 hours. After washing the plate 6 times with TBS-T, M13KO7 bacteriophage was diluted to a concentration of 3 µg/ml in TBS-T containing 3% BSA and dispensed by 100 µl per each well, and then reacted for 1 hour at room temperature. After washing the plate 3 times with TBS-T, an anti-M13 HRP conjugated antibody (Sino biological) was diluted to a concentration of 3 µg/ml in TBS-T containing 3% BSA and dispensed by 100 µl per each well, and then reacted for 1 hour at room temperature. After washing the plate 6 times, 100 µl of a TMB solution was added to each well to perform color development and after 10 minutes, 100 µl of 1 M sulfuric acid was added to stop the color development. Whether M13KO7 bacteriophage specifically detected PVY was quantitatively measured by a spectrophotometer.

As illustrated in FIG. 3, it was confirmed that the M13KO7 bacteriophage bacteriophage did not detect ChiVMV, PepMoV, PepSMV, PVA, PVV, PVMV, WMV and PPV belonging to other potyviruses. Therefore, it was confirmed that only the PVY was specifically detected and thus the specificity and accuracy for PVY was excellent.

What is claimed is:

1. A method for detecting a potato virus Y (PVY) comprising:

reacting a composition comprising at least one amino acid sequence selected from the group consisting of SEQ ID NO: 1, SEQ ID NO: 2, SEQ ID NO: 3, SEQ ID NO: 4, and SEQ ID NO: 5 with a desired sample comprising the PVY; and confirming a binding of the at least one amino acid sequence with the PVY.

2. The method of claim 1, wherein the sample is at least one selected from the group consisting of potato (*Solanum* sp.), eggplant (*Solanum* sp.), tobacco (*Nicotiana* sp.), tomato (*Lycopersicon* sp.), pepper (*Capsicum* sp.), dahlia (*Dahlia* sp.) and petunia.

3. The method of claim 1, wherein the confirming is performed by at least one selected from the group consisting of enzyme-linked immunosorbent assay (ELISA), western blotting, immunofluorescence, immunohistochemistry staining, flow cytometry, immunocytochemistry, radioimmunoassay (RIA), immunoprecipitation assay, immunodiffusion assay, complement fixation assay, and protein chips.

* * * * *

SEQUENCE LISTING

<160> NUMBER OF SEQ ID NOS: 11

<210> SEQ ID NO 1
<211> LENGTH: 424
<212> TYPE: PRT
<213> ORGANISM: Artificial Sequence
<220> FEATURE:
<223> OTHER INFORMATION: amino acid of M13KO7 bacteriophage gene 3

<400> SEQUENCE: 1

```
Met Lys Lys Leu Leu Phe Ala Ile Pro Leu Val Val Pro Phe Tyr Ser
1               5                   10                  15

His Ser Ala Glu Thr Val Glu Ser Cys Leu Ala Lys Pro His Thr Glu
            20                  25                  30

Asn Ser Phe Thr Asn Val Trp Lys Asp Asp Lys Thr Leu Asp Arg Tyr
        35                  40                  45

Ala Asn Tyr Glu Gly Cys Leu Trp Asn Ala Thr Gly Val Val Val Cys
    50                  55                  60

Thr Gly Asp Glu Thr Gln Cys Tyr Gly Thr Trp Val Pro Ile Gly Leu
65                  70                  75                  80

Ala Ile Pro Glu Asn Glu Gly Gly Gly Ser Glu Gly Gly Gly Ser Glu
                85                  90                  95

Gly Gly Gly Ser Glu Gly Gly Thr Lys Pro Pro Glu Tyr Gly Asp
                100                 105                 110

Thr Pro Ile Pro Gly Tyr Thr Tyr Ile Asn Pro Leu Asp Gly Thr Tyr
            115                 120                 125

Pro Pro Gly Thr Glu Gln Asn Pro Ala Asn Pro Asn Pro Ser Leu Glu
130                 135                 140

Glu Ser Gln Pro Leu Asn Thr Phe Met Phe Gln Asn Asn Arg Phe Arg
145                 150                 155                 160

Asn Arg Gln Gly Ala Leu Thr Val Tyr Thr Gly Thr Val Thr Gln Gly
                165                 170                 175

Thr Asp Pro Val Lys Thr Tyr Tyr Gln Tyr Thr Pro Val Ser Ser Lys
            180                 185                 190

Ala Met Tyr Asp Ala Tyr Trp Asn Gly Lys Phe Arg Asp Cys Ala Phe
        195                 200                 205

His Ser Gly Phe Asn Glu Asp Pro Phe Val Cys Glu Tyr Gln Gly Gln
    210                 215                 220

Ser Ser Asp Leu Pro Gln Pro Pro Val Asn Ala Gly Gly Gly Ser Gly
225                 230                 235                 240

Gly Gly Ser Gly Gly Gly Ser Glu Gly Gly Ser Glu Gly Gly
                245                 250                 255

Ser Glu Gly Gly Gly Ser Glu Gly Gly Ser Gly Gly Ser Gly
            260                 265                 270

Ser Gly Asp Phe Asp Tyr Glu Lys Met Ala Asn Ala Asn Lys Gly Ala
        275                 280                 285

Met Thr Glu Asn Ala Asp Glu Asn Ala Leu Gln Ser Asp Ala Lys Gly
    290                 295                 300

Lys Leu Asp Ser Val Ala Thr Asp Tyr Gly Ala Ala Ile Asp Gly Phe
305                 310                 315                 320

Ile Gly Asp Val Ser Gly Leu Ala Asn Gly Asn Gly Ala Thr Gly Asp
                325                 330                 335

Phe Ala Gly Ser Asn Ser Gln Met Ala Gln Val Gly Asp Gly Asp Asn
            340                 345                 350

Ser Pro Leu Met Asn Asn Phe Arg Gln Tyr Leu Pro Ser Leu Pro Gln
```

```
                355                 360                 365
Ser Val Glu Cys Arg Pro Phe Val Phe Ser Ala Gly Lys Pro Tyr Glu
    370                 375                 380

Phe Ser Ile Asp Cys Asp Lys Ile Asn Leu Phe Arg Gly Val Phe Ala
385                 390                 395                 400

Phe Leu Leu Tyr Val Ala Thr Phe Met Tyr Val Phe Ser Thr Phe Ala
                405                 410                 415

Asn Ile Leu Arg Asn Lys Glu Ser
            420

<210> SEQ ID NO 2
<211> LENGTH: 112
<212> TYPE: PRT
<213> ORGANISM: Artificial Sequence
<220> FEATURE:
<223> OTHER INFORMATION: amino acid of M13K07 bacteriophage gene 6

<400> SEQUENCE: 2

Met Pro Val Leu Leu Gly Ile Pro Leu Leu Arg Phe Leu Gly Phe
1               5                   10                  15

Leu Leu Val Thr Leu Phe Gly Tyr Leu Leu Thr Phe Leu Lys Lys Gly
            20                  25                  30

Phe Gly Lys Ile Ala Ile Ala Ile Ser Leu Phe Leu Ala Leu Ile Ile
        35                  40                  45

Gly Leu Asn Ser Ile Leu Val Gly Tyr Leu Ser Asp Ile Ser Ala Gln
    50                  55                  60

Leu Pro Ser Asp Phe Val Gln Gly Val Gln Leu Ile Leu Pro Ser Asn
65                  70                  75                  80

Ala Leu Pro Cys Phe Tyr Val Ile Leu Ser Val Lys Ala Ala Ile Phe
                85                  90                  95

Ile Phe Asp Val Lys Gln Lys Ile Val Ser Tyr Leu Asp Trp Asp Lys
            100                 105                 110

<210> SEQ ID NO 3
<211> LENGTH: 33
<212> TYPE: PRT
<213> ORGANISM: Artificial Sequence
<220> FEATURE:
<223> OTHER INFORMATION: amino acid of M13K07 bacteriophage gene 7

<400> SEQUENCE: 3

Met Glu Gln Val Ala Asp Phe Asp Thr Ile Tyr Gln Ala Met Ile Gln
1               5                   10                  15

Ile Ser Val Val Leu Cys Phe Ala Leu Gly Ile Ile Ala Gly Gly Gln
            20                  25                  30

Arg

<210> SEQ ID NO 4
<211> LENGTH: 73
<212> TYPE: PRT
<213> ORGANISM: Artificial Sequence
<220> FEATURE:
<223> OTHER INFORMATION: amino acid of M13K07 bacteriophage gene 8

<400> SEQUENCE: 4

Met Lys Lys Ser Leu Val Leu Lys Ala Ser Val Ala Val Ala Thr Leu
1               5                   10                  15

Val Pro Met Leu Ser Phe Ala Ala Glu Gly Asp Asp Pro Ala Lys Ala
            20                  25                  30
```

```
Ala Phe Asn Ser Leu Gln Ala Ser Ala Thr Glu Tyr Ile Gly Tyr Ala
         35                  40                  45

Trp Ala Met Val Val Val Ile Val Gly Ala Thr Ile Gly Ile Lys Leu
 50                  55                  60

Phe Lys Lys Phe Thr Ser Lys Ala Ser
 65                  70

<210> SEQ ID NO 5
<211> LENGTH: 32
<212> TYPE: PRT
<213> ORGANISM: Artificial Sequence
<220> FEATURE:
<223> OTHER INFORMATION: amino acid of M13KO7 bacteriophage gene 9

<400> SEQUENCE: 5

Met Ser Val Leu Val Tyr Ser Phe Ala Ser Phe Val Leu Gly Trp Cys
  1               5                  10                  15

Leu Arg Ser Gly Ile Thr Tyr Phe Thr Arg Leu Met Glu Thr Ser Ser
             20                  25                  30

<210> SEQ ID NO 6
<211> LENGTH: 1275
<212> TYPE: DNA
<213> ORGANISM: Artificial Sequence
<220> FEATURE:
<223> OTHER INFORMATION: M13KO7 bacteriophage gene 3

<400> SEQUENCE: 6
atgaaaaaat tattattcgc aattccttta gttgttcctt tctattctca ctccgctgaa      60
actgttgaaa gttgtttagc aaaaccccat acagaaaatt catttactaa cgtctggaaa     120
gacgacaaaa ctttagatcg ttacgctaac tatgagggtt gtctgtggaa tgctacaggc     180
gttgtagttt gtactggtga cgaaactcag tgttacggta catgggttcc tattgggctt     240
gctatccctg aaaatgaggg tggtggctct gagggtggcg gttctgaggg tggcggttct     300
gagggtggcg gtactaaacc tcctgagtac ggtgatacac ctattccggg ctatacttat     360
atcaaccctc tcgacggcac ttatccgcct ggtactgagc aaaacccgc taatcctaat     420 ccttctcttg aggagtctca gcctcttaat actttcatgt ttcagaataa taggttccga     480
aataggcagg ggcattaac tgtttatacg ggcactgtta ctcaaggcac tgaccccgtt     540
aaaacttatt accagtacac tcctgtatca tcaaaagcca tgtatgacgc ttactggaac     600
ggtaaattca gagactgcgc tttccattct ggctttaatg aggatccatt cgtttgtgaa     660
tatcaaggcc aatcgtctga cctgcctcaa cctcctgtca atgctggcgg cggctctggt     720
ggtggttctg gtggcggctc tgagggtggt ggctctgagg gtggcggttc tgagggtggc     780
ggctctgagg gaggcggttc cggtggtggc tctggttccg gtgattttga ttatgaaaag     840
atggcaaacg ctaataaggg ggctatgacc gaaaatgccg atgaaaacgc gctacagtct     900
gacgctaaag gcaaacttga ttctgtcgct actgattacg gtgctgctat cgatggtttc     960
attggtgacg tttccggcct tgctaatggt aatggtgcta ctggtgattt tgctggctct    1020
aattcccaaa tggctcaagt cggtgacggt gataattcac ctttaatgaa taatttccgt    1080
caatatttac cttccctccc tcaatcggtt gaatgtcgcc cttttgtctt tagcgctggt    1140
aaaccatatg aattttctat tgattgtgac aaaataaact tattccgtgg tgtctttgcg    1200
tttcttttat atgttgccac ctttatgtat gtattttcta cgtttgctaa catactgcgt    1260
aataaggagt cttaa                                                      1275
```

<210> SEQ ID NO 7
<211> LENGTH: 339
<212> TYPE: DNA
<213> ORGANISM: Artificial Sequence
<220> FEATURE:
<223> OTHER INFORMATION: M13KO7 bacteriophage gene 6

<400> SEQUENCE: 7

| | |
|---|---|
| atgccagttc ttttgggtat tccgttatta ttgcgtttcc tcggtttcct tctggtaact | 60 |
| ttgttcggct atctgcttac ttttcttaaa aagggcttcg gtaagatagc tattgctatt | 120 |
| tcattgtttc ttgctcttat tattgggctt aactcaattc ttgtgggtta tctctctgat | 180 |
| attagcgctc aattacccctc tgactttgtt cagggtgttc agttaattct cccgtctaat | 240 |
| gcgcttccct gtttttatgt tattctctct gtaaaggctg ctattttcat ttttgacgtt | 300 |
| aaacaaaaaa tcgtttctta tttggattgg gataaataa | 339 |

<210> SEQ ID NO 8
<211> LENGTH: 102
<212> TYPE: DNA
<213> ORGANISM: Artificial Sequence
<220> FEATURE:
<223> OTHER INFORMATION: M13KO7 bacteriophage gene 7

<400> SEQUENCE: 8

| | |
|---|---|
| atggagcagg tcgcggattt cgacacaatt tatcaggcga tgatacaaat ctccgttgta | 60 |
| ctttgtttcg cgcttggtat aatagctggg ggtcaaagat ga | 102 |

<210> SEQ ID NO 9
<211> LENGTH: 222
<212> TYPE: DNA
<213> ORGANISM: Artificial Sequence
<220> FEATURE:
<223> OTHER INFORMATION: M13KO7 bacteriophage gene 8

<400> SEQUENCE: 9

| | |
|---|---|
| atgaaaaagt ctttagtcct caaagcctct gtagccgttg ctaccctcgt tccgatgctg | 60 |
| tctttcgctg ctgagggtga cgatcccgca aaagcggcct ttaactccct gcaagcctca | 120 |
| gcgaccgaat atatcggtta tgcgtgggcg atggttgttg tcattgtcgg cgcaactatc | 180 |
| ggtatcaagc tgtttaagaa attcacctcg aaagcaagct ga | 222 |

<210> SEQ ID NO 10
<211> LENGTH: 99
<212> TYPE: DNA
<213> ORGANISM: Artificial Sequence
<220> FEATURE:
<223> OTHER INFORMATION: M13KO7 bacteriophage gene 9

<400> SEQUENCE: 10

| | |
|---|---|
| atgagtgttt tagtgtattc tttcgcctct ttcgttttag gttggtgcct tcgtagtggc | 60 |
| attacgtatt tacccgtttt aatggaaact tcctcatga | 99 |

<210> SEQ ID NO 11
<211> LENGTH: 8669
<212> TYPE: DNA
<213> ORGANISM: Artificial Sequence
<220> FEATURE:
<223> OTHER INFORMATION: M13KO7 bacteriophage gene

<400> SEQUENCE: 11

| | |
|---|---|
| aacgctacta ctattagtag aattgatgcc accttttcag ctcgcgcccc aaatgaaaat | 60 |

-continued

```
atagctaaac aggttattga ccatttgcga aatgtatcta atggtcaaac taaatctact      120
cgttcgcaga attgggaatc aactgttaca tggaatgaaa cttccagaca ccgtactttg      180
gttgcatatt taaaacatgt tgagctacag caccagattc agcaattaag ctctaagcca      240
tccgcaaaaa tgacctctta tcaaaaggag caattaaagg tactctctaa tcctgacctg      300
ttggagtttg cttccggtct ggttcgcttt gaagctcgaa ttaaaacgcg atatttgaag      360
tctttcgggc ttcctcttaa tcttttgat gcaatccgct ttgcttctga ctataatagt       420
cagggtaaag acctgatttt tgatttatgg tcattctcgt tttctgaact gtttaaagca      480
tttgagggga attcaatgaa tatttatgac gattccgcag tattggacgc tatccagtct      540
aaacatttta ctattacccc ctctggcaaa acttcttttg caaaagcctc tcgctatttt      600 ggttttatc gtcgtctggt aaacgagggt tatgatagtg ttgctcttac tatgcctcgt       660
aattcctttt ggcgttatgt atctgcatta gttgaatgtg gtattcctaa atctcaactg      720
atgaatcttt ctacctgtaa taatgttgtt ccgttagttc gttttattaa cgtagatttt      780
tcttcccaac gtcctgactg gtataatgag ccagttctta aaatcgcata aggtaattca      840
caatgattaa agttgaaatt aaaccatctc aagcccaatt tactactcgt tctggtgttt      900
ctcgtcaggg caagccttat tcactgaatg agcagctttg ttacgttgat ttgggtaatg      960
aatatccggt tcttgtcaag attactcttg atgaaggtca gccagcctat gcgcctggtc     1020
tgtacaccgt tcatctgtcc tctttcaaag ttggtcagtt cggttccctt atgattgacc     1080
gtctgcgcct cgttccggct aagtaacatg gagcaggtcg cggatttcga cacaattta     1140 caggcgatga tacaaatctc cgttgtactt tgtttcgcgc ttggtataat cgctggggt      1200 caaagatgag tgttttagtg tattctttcg cctctttcgt tttaggttgg tgccttcgta     1260
gtggcattac gtattttacc cgtttaatgg aaacttcctc atgaaaaagt ctttagtcct     1320
caaagcctct gtagccgttg ctaccctcgt tccgatgctg tctttcgctg ctgagggtga     1380
cgatcccgca aaagcggcct ttaactccct gcaagcctca gcgaccgaat atatcggtta     1440
tgcgtgggcg atggttgttg tcattgtcgg cgcaactatc ggtatcaagc tgtttaagaa     1500
attcacctcg aaagcaagct gataaaccga tacaattaaa ggctcctttt ggagcctttt     1560 ttttggaga ttttcaacgt gaaaaaatta ttattcgcaa ttcctttagt tgttcctttc      1620
tattctcact ccgctgaaac tgttgaaagt tgtttagcaa acccatac agaaaattca       1680 tttactaacg tctggaaaga cgacaaaact ttagatcgtt acgctaacta tgagggttgt     1740
ctgtggaatg ctacaggcgt tgtagtttgt actggtgacg aaactcagtg ttacggtaca     1800
tgggttccta ttgggcttgc tatccctgaa aatgagggtg gtggctctga gggtggcggt     1860
tctgagggtg gcggttctga gggtggcggt actaaacctc ctgagtacgg tgatacacct     1920
attccgggct atacttatat caaccctctc gacggcactt atccgcctgg tactgagcaa     1980
aaccccgcta atcctaatcc ttctcttgag gagtctcagc ctcttaatac tttcatgttt     2040
cagaataata ggttccgaaa taggcagggg gcattaactg tttatacggg cactgttact     2100
caaggcactg accccgttaa aacttattac cagtacactc ctgtatcatc aaaagccatg     2160
tatgacgctt actggaacgg taaattcaga gactgcgctt ccattctggc tttaatgag      2220 gatccattcg tttgtgaata tcaaggccaa tcgtctgacc tgcctcaacc tcctgtcaat     2280 gctgcggcg ctctggtgg tggttctggt ggcggctctg agggtggtgg ctctgagggt       2340
ggcggttctg agggtggcgg ctctgaggga ggcggttccg gtggtggctc tggttccggt     2400
```

```
gattttgatt atgaaaagat ggcaaacgct aataaggggg ctatgaccga aaatgccgat    2460
gaaaacgcgc tacagtctga cgctaaaggc aaacttgatt ctgtcgctac tgattacggt    2520
gctgctatcg atggtttcat tggtgacgtt tccggccttg ctaatggtaa tggtgctact    2580
ggtgattttg ctggctctaa ttcccaaatg gctcaagtcg gtgacggtga taattcacct    2640
ttaatgaata atttccgtca atatttacct tccctccctc aatcggttga atgtcgccct    2700
tttgtcttta gcgctggtaa accatatgaa ttttctattg attgtgacaa aataaactta    2760
ttccgtggtg tctttgcgtt tcttttatat gttgccacct ttatgtatgt attttctacg    2820
tttgctaaca tactgcgtaa taaggagtct aatcatgcca gttcttttg ggtattccgt    2880 tattattgcg tttcctcggt ttccttctgg taactttgtt cggctatctg cttacttttc    2940
ttaaaaaggg cttcggtaag atagctattg ctatttcatt gtttcttgct cttattattg    3000
ggcttaactc aattcttgtg ggttatctct ctgatattag cgctcaatta ccctctgact    3060
ttgttcaggg tgttcagtta attctcccgt ctaatgcgct tccctgtttt tatgttattc    3120
tctctgtaaa ggctgctatt ttcattttg acgttaaaca aaaaatcgtt tcttatttgg    3180
attgggataa ataatatggc tgtttatttt gtaactggca aattaggctc tggaaagacg    3240
ctcgttagcg ttggtaagat tcaggataaa attgtagctg ggtgcaaaat agcaactaat    3300
cttgatttaa ggcttcaaaa cctcccgcaa gtcgggaggt tcgctaaaac gcctcgcgtt    3360
cttagaatac cggataagcc ttctatatct gatttgcttg ctattgggcg cggtaatgat    3420
tcctacgatg aaaataaaaa cggcttgctt gttctcgatg agtgcggtac ttggtttaat    3480
acccgttctt ggaatgataa ggaaagacag ccgattattg attggtttct acatgctcgt    3540
aaattaggat gggatattat ttttcttgtt caggacttat ctattgttga taaacaggcg    3600
cgttctgcat tagctgaaca tgttgtttat tgtcgtcgtc tggacagaat tactttacct    3660
tttgtcggta ctttatattc tcttattact ggctcgaaaa tgcctctgcc taaattacat    3720
gttggcgttg ttaaatatgg cgattctcaa ttaagcccta ctgttgagcg ttggctttat    3780
actggtaaga atttgtataa cgcatatgat actaaacagg ctttttctag taattatgat    3840
tccggtgttt attcttattt aacgccttat ttatcacacg gtcggtattt caaaccatta    3900
aatttaggtc agaagatgaa attaactaaa atatatttga aaaagttttc tcgcgttctt    3960
tgtcttgcga ttggatttgc atcagcattt acatatagtt atataaccca acctaagccg    4020
gaggttaaaa aggtagtctc tcagacctat gattttgata aattcactat tgactcttct    4080
cagcgtctta atctaagcta tcgctatgtt ttcaaggatt ctaagggaaa attaattaat    4140
agcgacgatt tacagaagca aggttattca ctcacatata ttgatttatg tactgtttcc    4200
attaaaaaag gtaattcaaa tgaaattgtt aaatgtaatt aattttgttt tcttgatgtt    4260
tgtttcatca tcttcttttg ctcaggtaat tgaaatgaat aattcgcctc tgcgcgattt    4320
tgtaacttgg tattcaaagc aatcaggcga atccgttatt gtttctcccg atgtaaaagg    4380
tactgttact gtatattcat ctgacgttaa acctgaaaat ctacgcaatt tctttatttc    4440
tgttttacgt gctaataatt ttgatatggt tggttcaatt ccttccataa ttcagaagta    4500
taatccaaac aatcaggatt atattgatga attgccatca tctgataatc aggaatatga    4560
tgataattcc gctccttctg gtggtttctt tgttccgcaa aatgataatg ttactcaaac    4620
ttttaaaatt aataacgttc gggcaaagga tttaatacga gttgtcgaat tgtttgtaaa    4680
gtctaatact tctaaatcct caaatgtatt atcattgac ggctcaatc tattagttgt    4740 tagtgcacct aaagatattt tagataacct tcctcaattc ctttctactg ttgatttgcc    4800
```

-continued

```
aactgaccag atattgattg agggtttgat atttgaggtt cagcaaggtg atgctttaga    4860
tttttcattt gctgctggct ctcagcgtgg cactgttgca ggcggtgtta atactgaccg    4920
cctcacctct gttttatctt ctgctggtgg ttcgttcggt attttttaatg gcgatgtttt   4980
agggctatca gttcgcgcat taaagactaa tagccattca aaatattgt ctgtgccacg     5040
tattcttacg ctttcaggtc agaagggttc tatctctgtt ggccagaatg tcccttttat    5100
tactggtcgt gtgactggtg aatctgccaa tgtaaataat ccatttcaga cgattgagcg    5160
tcaaaatgta ggtatttcca tgagcgtttt tcctgttgca atggctggcg gtaatattgt    5220
tctggatatt accagcaagg ccgatagttt gagttcttct actcaggcaa gtgatgttat    5280
tactaatcaa agaagtattg ctacaacggt taatttgcgt gatggacaga ctcttttact    5340
cggtggcctc actgattata aaacacttc tcaagattct ggcgtaccgt tcctgtctaa     5400
aatcccttta atcggcctcc tgtttagctc ccgctctgat tccaacgagg aaagcacgtt    5460
atacgtgctc gtcaaagcaa ccatagtacg cgccctgtag cggcgcatta agcgcggcgg   5520
gtgtggtggt tacgcgcagc gtgaccgcta cacttgccag cgccctagcg cccgctcctt    5580
tcgctttctt cccttccttt ctcgccacgt tcgccggctt tccccgtcaa gctctaaatc    5640
ggggctccc tttagggttc cgatttagtg ctttacggca cctcgacccc aaaaaacttg    5700
atttgggtga tggttcacgt agtgggccat cgccctgata acggtttttt cgccctttga   5760
cgttggagtc cacgttcttt aatagtggac tcttgttcca aactgaaaca acactcaacc   5820
ctatctcggg acgatcgct tcatgtgca ggagaaaaaa ggctcaccg gtgcgtcagc       5880
agaatatgtg atacaggata tattccgctt cctcgctcac tgactcgcta cgctcggtcg    5940
ttcgactgcg gcgagcggaa atggcttacg aacggggcgg agatttcctg gaagatgcca    6000
ggaagatact taacagggaa gtgagagggc gcggcaaag ccgttttttcc ataggctccg    6060
ccccccctgac aagcatcacg aaatctgacg ctcaaatcag tggtggcgaa acccgacagg  6120
actataaaga taccaggcgt ttccccctgg cggctccctc gtgcgctctc ctgttcctgc    6180
ctttcggttt accggtgtca ttccgctgtt atggccgcgt ttgtctcatt ccacgcctga   6240
cactcagttc cgggtaggca gttcgctcca agctggactg tatgcacgaa ccccccgttc   6300
agtccgaccg ctgcgcctta tccggtaact atcgtcttga gtccaacccg gaaagacatg   6360
caaaagcacc actggcagca gccactggta attgatttag aggagttagt cttgaagtca   6420
tgcgccggtt aaggctaaac tgaaaggaca gttttggtg actgcgctcc tccaagccag    6480
ttacctcggt tcaaagagtt ggtagctcag agaaccttcg aaaaaccgcc ctgcaaggcg   6540
gttttttcgt tttcagagca agagattacg cgcagaccaa aacgatctca agaagatcat    6600
cttattaagg ggtctgacgc tcagtggaac gaaaactcac gttaagggat ttggtcatg     6660
agattatcaa aaaggatctt cacctagatc ctttttaaatt aaaaatgaag ttttaaatca  6720
atctaaagta tatatgagta aacttggtct gacagttacc aatgcttaat cagtgaggca   6780
cctatctcag cgatctgtct atttcgttca tccatagttg cctgactccc cgtcgtgtag   6840
ataactacga tacgggaggg cttaccatct ggccccagtg ctgcaatgat accgcgagac    6900
ccacgctcac cggctccaga tttatcagca ataaaccagc cagccgattc gagctcgccc   6960
cggggatcga ccagttggtg attttgaact tttgctttgc cacggaacgg tctgcgttgt    7020
cgggaagatg cgtgatctga tccttcaact cagcaaaagt tcgatttatt caacaaagcc   7080
gccgtcccgt caagtcagcg taatgctctg ccagtgttac aaccaattaa ccaattctga   7140
```

-continued

```
ttagaaaaac tcatcgagca tcaaatgaaa ctgcaattta ttcatatcag gattatcaat   7200
accatatttt tgaaaaagcc gtttctgtaa tgaaggagaa aactcaccga ggcagttcca   7260
taggatggca agatcctggt atcggtctgc gattccgact cgtccaacat caatacaacc   7320
tattaatttc ccctcgtcaa aaataaggtt atcaagtgag aaatcaccat gagtgacgac   7380
tgaatccggt gagaatggca aaagcttatg catttctttc cagacttgtt caacaggcca   7440
gccattacgc tcgtcatcaa aatcactcgc atcaaccaaa ccgttattca ttcgtgattg   7500
cgcctgagcg agacgaaata cgcgatcgct gttaaaagga caattacaaa caggaatcga   7560
atgcaaccgg cgcaggaaca ctgccagcgc atcaacaata ttttcacctg aatcaggata   7620
ttcttctaat acctggaatg ctgttttccc ggggatcgca gtggtgagta accatgcatc   7680
atcaggagta cggataaaat gcttgatggt cggaagaggc ataaattccg tcagccagtt   7740
tagtctgacc atctcatctg taacatcatt ggcaacgcta cctttgccat gtttcagaaa   7800
caactctggc gcatcgggct tcccatacaa tcgatagatt gtcgcacctg attgcccgac   7860
attatcgcga gcccatttat acccatataa atcagcatcc atgttggaat ttaatcgcgg   7920
cctcgagcaa gacgtttccc gttgaatatg gctcataaca ccccttgtat tactgtttat   7980
gtaagcagac agttttattg ttcatgatga tatattttta tcttgtgcaa tgtaacatca   8040
gagattttga gacacaacgt ggctttcccc ccccccccct gcaggtctcg ggctattctt   8100
ttgatttata agggattttg ccgatttcgg cctattggtt aaaaaatgag ctgatttaac   8160
aaaaatttaa cgcgaatttt aacaaaatat taacgtttac aatttaaata tttgcttata   8220
caatcttcct gtttttgggg cttttctgat tatcaaccgg ggtacatatg attgacatgc   8280
tagttttacg attaccgttc atcgattctc ttgtttgctc cagactctca ggcaatgacc   8340
tgatagcctt tgtagacctc tcaaaaatag ctaccctctc cggcatgaat ttatcagcta   8400
gaacggttga atatcatatt gatggtgatt tgactgtctc cggcctttct caccctttg    8460
aatctttacc tacacattac tcaggcattg catttaaaat atatgagggt tctaaaaatt   8520
tttatccttg cgttgaaata aaggcttctc ccgcaaaagt attacagggt cataatgttt   8580
ttggtacaac cgatttagct ttatgctctg aggctttatt gcttaatttt gctaattctt   8640
tgccttgcct gtatgattta ttggatgtt                                    8669
```